United States Patent [19]

Sawano et al.

[11] Patent Number: 5,141,921

[45] Date of Patent: Aug. 25, 1992

[54] PERFUME COMPOSITION

[75] Inventors: Kiyohito Sawano; Kenya Ishida; Akemi Shimada, all of Tokyo, Japan

[73] Assignee: Takasago International Corporation, Tokyo, Japan

[21] Appl. No.: 683,911

[22] Filed: Apr. 11, 1991

[30] Foreign Application Priority Data

Apr. 13, 1990 [JP] Japan ................................. 2-96189

[51] Int. Cl.$^5$ .............................................. A61K 7/46
[52] U.S. Cl. ...................................................... 512/26
[58] Field of Search ........................................ 512/26

[56] References Cited

U.S. PATENT DOCUMENTS 3,579,550  5/1971  Demole ................. 512/26
4,609,492  9/1986  Hata et al. ............. 512/26

FOREIGN PATENT DOCUMENTS 3225293  1/1984  Fed. Rep. of Germany ........ 512/26

OTHER PUBLICATIONS

Smith et al., Science, vol. 166, pp. 398–399 (1969).
Gordon et al., J. of Lipid Research, vol. 14, pp. 495–503 (1973).
Smith et al., J. of Pharmaceutical Sciences, vol. 61, pp. 316–317 (1972).
Wohlberg et al., Phytochemistry, vol. 16, pp. 1217–1231 (1977).
De Rijke et al., Phytochemistry, vol. 17, pp. 1664–1666 (1978).
Moy et al., J. of American Oil Chemists' Society, vol. 60, pp. 990–995 (1983).

*Primary Examiner*—James H. Reamer
*Attorney, Agent, or Firm*—Sughrue, Mion, Zinn, Macpeak & Seas

[57] ABSTRACT

A perfume composition containing 3-methyl-2-hexenoic acid and/or 7-octenoic acid is disclosed. The perfume composition has a fresh and natural animal note and excellent diffusibility and tastiness. The perfume composition produces psychological effects on humans, such as an awakening effect and/or a sedative effect.

2 Claims, No Drawings

PERFUME COMPOSITION

FIELD OF THE INVENTION

This invention relates to a perfume composition and, more particularly to a perfume composition containing 3-methyl-2-hexenoic acid and/or 7-octenoic acid. 3-Methyl-2-hexenoic acid and 7-octenoic acid are compounds giving a novel animal note, and the perfume composition containing the same according to this invention is effectively useful in perfuming goods, e.g., perfumes, eau de Cologne, and cosmetics; aromatics; and sanitary goods.

BACKGROUND OF THE INVENTION

In compounding fine fragrances, animal perfumes, such as musk, civet and castreum, have hitherto been highly valued as natural perfuming substances emitting an animal note. On the other hand, human body smell is known to be ascribed to volatile lower fatty acids, e.g., isovaleric acid, butyric acid, isobutyric acid, propionic acid, and acetic acid. Since any of these fatty acids gives off an unpleasant smell of sweat, various measures have ever been taken for body deodorization. Further, steroids, e.g., androstenol and androsterone, are detected from human perspiration or urine and known as one of causes of body odor. However, these steroids possess hormone activities and are therefore limited in their use as perfumes.

3-Methyl-2-hexenoic acid, which is used in the perfume composition of the present invention, embraces steric isomers, (E)-compound and (Z)-compound, in nature of its chemical structure. The (E)-compound was isolated for the first time from the sweat of schizophrenic patients as a substance causing a peculiar offensive odor (see,, K. Smith et al., *Science*, Vol. 166, pp. 398–399 (1969)) and then found to be also present in the sweat of healthy persons in an equal amount and so to have nothing with schizophrenia (see S. G. Gordon et al., *Journal of Lipid Research*, Vol. 14, pp. 495–503 (1973)). It was also reported that a mixture of the (E)-compound and (Z)-compound was obtained through synthesis (see R. V. Smith et al., *Journal of Pharmaceutical Sciences*, Vol. 61, pp. 316–317 (1972)). Any of these reports only describes that the odor of 3-methyl-2-hexenoic acid is offensive, giving no suggestion as to utility as a perfume.

On the other hand, 7-octenoic acid was reported to be present in tobacco or an essential oil of olibanum (see I. Wahlberg et al., *Phytochemistry*, Vol. 16, pp. 1217–1231 (1977) and D. De Rijke et al., *Phytochemistry*, Vol. 17, pp. 1664–1666 (1978)). It was also reported to be obtained by pyrolysis of triolein (see W. A. May et al., *Journal of American Oil Chemists' Society*, Vol. 60, pp. 990–995 (1983)). None of these reports describes about the perfume of 7-octenoic acid, still leaving utility as a perfume unknown. Further, JP-A-61-254515 (the term "JP-A" as used herein means an "unexamined published Japanese patent application") discloses a perfume composition having a smell of Chinese quince which contains a 7-octenoic acid ester and teaches synthesis of 7-octenoic acid as an intermediate of its ester but gives no disclosure on the odor of 7-octenoic acid itself, still less on utility as a perfume.

The above-mentioned musk, civet, castreum, etc. that have conventionally been used as perfumes offering an animal note are getting hardly obtainable for reservation of animals. It has hence been demanded to develop an animal note-giving perfume material which is easily available from origins except animals and still has a fresh and natural odor with excellent diffusibility and tastiness.

With the recent diversity of perfuming cosmetics, aromatics and sanitary goods, there has been an increasing need to offer these goods with a unique scent. Further, so-called aromatherapy in which aromatic substances such as perfumes are used for mental and physical control has recently been attracting attention, and development of perfume compositions having such functions has been demanded.

SUMMARY OF THE INVENTION

An object of the present invention is to provide a perfume composition satisfying all these demands.

Paying attention to a possibility of human body odor which has been regarded offensive as a material of perfume having an animal note, the inventors separated body odor into components and found that 3-methyl-2-hexenoic acid and 7-octenoic acid of the separated components have a very strong animal note. Based on this finding, they synthesized these compounds and conducted odor tests. As a result, it has now been found that 3-methyl-2-hexenoic acid and 7-octenoic acid can be a useful animal base which, when compounded into mixed perfumes having an animal-like, amber-like, or balsam-like keynote, makes the odor fresher and more natural and enhances diffusibility and tastiness. Besides being safe to human body as originally possessed by humans, 3-methyl-2-hexenoic acid and 7-octenoic acid are expected to have psychological effects, for example, sexual effects; i.e., they are expected to perform some important function in human relationship. The inventors thus studied on psychological influences of these compounds upon humans and, as a result, found that they have a sedative effect and/or an awakening effect. The present invention has been completed based on these findings.

That is, the present invention relates to a perfume composition containing 3-methyl-2-hexenoic acid and/or 7-octenoic acid.

DETAILED DESCRIPTION OF THE INVENTION

3-Methyl-2-hexenoic acid and 7-octenoic acid which can be used in the present invention are original components of human body odor and can be isolated from the secretion of human skin or synthetically obtained with ease. For example, 3-methyl-2-hexenoic acid can be synthesized by Wittig reaction between a Wittig reagent prepared from, e.g., ethyl chloroacetate and n-propyl methyl ketone, followed by hydrolysis. 7-Octenoic acid can be synthesized by reacting 5-hexenyl chloride obtainable from 5-hexenol with diethyl malonate, hydrolyzing the product with an alkali, and decarboxylating the hydrolysis product with an acid as described, e.g., in JP-A-61-254515.

As stated above, 3-methyl-2-hexenoic acid includes an (E)-compound and a (Z)-compound in nature of its chemical structure. While the compound isolated from the secretion of human skin was identified to be the (E)-compound, the synthetically obtained species is a mixture comprising about 80% of the (E)-compound and about 20% of the (Z)-compound. The odor of the (E)/(Z) isomeric mixture was confirmed to have a strongly diffusible animal note, which almost agreed with the odor of the compound isolated from the secretion of human skin. That is, unless a very slight difference in scent has importance in compounding technique, the (E)/(Z) isomeric mixture as synthetically produced can be used as such in the present invention without being separated into each isomers. This does not mean to exclude use of each of separated isomers or an arbitrary mixture of separated isomers. In any case, 3-methyl-2-hexenoic acid has an animal odor and particularly a civet-like or musk-like odor combined with woody, camphor-like, fatty, and fruity elements to give off, as a whole, a sexual odor. The delicate difference in odor between the (E)-isomer and the (Z)-isomer lies in that the latter feels slightly softer than the former.

Synthetic 7-octenoic acid was also confirmed to have a strongly diffusible animal note which agrees with that of the compound isolated from the secretion of human skin. This compound has an animal and fatty odor combined with amber-like, woody and fruity elements to give off, as a whole, a sexual odor.

The inventors examined influences of the thus obtained 3-methyl-2-hexenoic acid and 7-octenoic acid on humans according to the method proposed by Fukuda et al. in *Proceedings of The 19th Japanese Symposium on Taste and Smell*, edited by Japanese Association for the Study of Taste and Smell, pp. 65-68 (1985) (this method being hereinafter referred to as "Fukuda's method"). That is, the compounds according to the present invention were investigated for their awakening effect or sedative effect on humans with distinction of sex by using, as an indication of contingent negative variation (hereinafter abbreviated as CNV) which is a mild variation of cerebral potential in relation to psychic processes, such as attention, expectation, and prediction, or variations of consciousness level. As a result, 3-methyl-2-hexenoic acid manifested a sedative effect on females and an awakening effect on males, and 7-octenoic acid manifested an awakening effect on females and a sedative effect on males. From these results, a perfume composition containing 3-methyl-2-hexenoic acid is expected to produce a sedative effect on females and an awakening effect on males; and a perfume composition containing 7-octenoic acid is expected to produce an awakening effect on females and a sedative effect on males.

3-Methyl-2-hexenoic acid and 7-octenoic acid may be compounded into a perfume composition in expectation of such an awakening effect or a sedative effect either individually or as a mixture thereof in an arbitrary ratio for obtaining various tones. Since 3-methyl-2-hexenoic acid and 7-octenoic acid are both in good harmony with various synthetic or natural perfumes, synthetic or natural essential oils, and other perfuming materials, they can be compounded with these materials to provide a novel perfume composition. For example, they can be used as an animal base to prepare a perfume composition. In particular, they can be compounded into a mixed perfume having an animal, amber or balsam keynote to provide a perfume composition having a fresh and nearly natural odor with excellent diffusibility and tastiness.

The amount of 3-methyl-2-hexenoic acid and/or 7-octenoic acid to be compounded is selected appropriately depending on use. Usually, it is from 0.001 to 2% by weight, and preferably from 0.01 to 1% by weight, based on the whole perfume composition. In concentrations exceeding 2%, these compounds, particularly 3-methyl-2-hexenoic acid would emit an offensive armpit smell (hircismus)-like smell to make the composition rather unpleasant, failing to obtain a desired pleasant animal note. On the other hand, in concentrations less than 0.001%, no effect as a perfume is produced.

Thus, the perfume composition containing 3-methyl-2-hexenoic acid and/or 7-octenoic acid according to the present invention has a fresh and natural animal note excellent in diffusibility and tastiness. The perfume composition of the present invention is also expected to produce psychological effects on humans, such as an awakening effect and/or a sedative effect. Accordingly, the perfume composition of the invention is useful as an aromatic component of various cosmetics, aromatics, and sanitary goods. The perfume composition of the present invention can be incorporated in an amount effective to impart its unique odor to perfumes or eau de Cologne; bases of hair care cosmetics, e.g., shampoos, rinses, hair tonics, hair creams, pomades, etc.; bases of facial cosmetics, e.g., face powders, lip sticks, face cleansers, etc.; detergents, e.g., soaps, disinfectant detergents, laundry detergents, etc.; environmental aromatizers; bathing additives; and the like thereby to enhance the commercial value of these goods.

The present invention will now be illustrated in greater detail with reference to Synthesis Examples, CNV Test Example, CNV Test Reference Example, and Working Examples but it should be understood that the present invention is not deemed to be limited thereto. All the percents, parts, and ratios are by weight unless otherwise indicated.

SYNTHESIS EXAMPLE 1

Synthesis of 3-Methyl-2-hexenoic Acid

1) Synthesis of Wittig reagent:

In a flask were charged 900 ml of hexane and 42 g (1.83 mole) of sodium, and 250 g (1.81 mole) of diethyl phosphonate was added dropwise thereto at 20° to 40° C. over 2 hours. The mixture was stirred until sodium disappeared. Then, 277 g (2.22 mole) of ethyl chloroacetate was added dropwise over 1 hour, followed by refluxing for 1 hour. After stirring at room temperature overnight, the reaction mixture was filtered, and the filtrate was distilled under reduced pressure to obtain 255 g (yield: 63%) of a Wittig reagent (110° C./5 mmHg).

2) Wittig Reaction

In a flask were charged 1020 ml of toluene and 27 g (1.13 mole) of sodium hydroxide, and 255 g (1.14 mole) of the Wittig reagent obtained in (1) above was added dropwise at room temperature over 1 hour, followed by stirring for 1 hour. Then, 98 g (1.02 mole) of n-propyl methyl ketone was added dropwise thereto over 1 hour, followed by stirring at 35 to 40° C. for 2 hours to obtain 155 g (yield: 87%) of ethyl 3-methyl-2-hexenoate.

3) Hydrolysis

In a flask were charged 155 g (0.89 mole) of ethyl 3-methyl-2-hexenoate as obtained in (2) above, 112 g (2.00 mole) of potassium hydroxide, 633 g of water, and 1000 ml of methanol, and the mixture was refluxed for 3 hours. The reaction mixture was extracted with hexane, and the aqueous layer was washed with diluted hydrochloric acid and extracted with diethyl ether to obtain a concentrate weighing 110 g. The concentrate was distilled to obtain 46 g (yield: 36%) of the titled compound as a colorless oil.

The resulting product was found to have an (E)/(Z) isomer ratio of 79:21 as analyzed by gas chromatography under the following conditions.

Chromatograph: Model 263-50, produced by Hitachi, Ltd.

Column: PEG 20M (chemical bond type), 0.25 mm ×25 m

Temperature: kept constant at 150° C.

4) Measurement of Physical Properties

Physical properties of the resulting 3-methyl-2-hexenoic acid were measured with the following instruments.

IR: Model IR-810, manufactured by JASCO Inc.

$^1$H-NMR Model AM-400, manufactured by Bruker, Inc. (internal standard: tetramethylsilane)

MS: Model M-80B Mass Spectrometer, produced by Hitachi, Ltd. (ionizing voltage: 20 eV)

Results of Measurement:

i) (E)-Compound

IR (KBr) cm$^{-1}$: 3300–2500 (broad), 1690

$^1$H-NMR (CDCl$_3$) δ ppm: 0.92 (3H, t), 1.52 (2H, m), 2.15 (2H, t), 2.16 (3H, d), 5.70 (1H, s)

MS (m/e): 128 (M ), 122, 113, 100, 87, 81, 69, 55, 41, 28, 18 ii) (Z)-Compound

IR (KBr) cm$^{-1}$: 3300–2500 (broad), 1690

$^1$H-NMR (CDCl$_3$) δ ppm: 0.95 (3H, t), 1.50 (2H, m), 1.91 (3H, s), 2.62 (2H, dd), 5.69 (1H, s)

MS (m/e): 128 (M+), 113, 110, 87, 81, 69, 55, 43, 27, 18

SYNTHESIS EXAMPLE 2

Synthesis of 7-Octenoic Acid

1) Synthesis of 5-Hexenyl Chloride

To a solution of 18 g (0.18 mole) of 5-hexenol in 300 ml of anhydrous carbon tetrachloride was added 55 g (0.21 mole) of triphenylphosphine, followed by refluxing with stirring for 1 hour. The reaction mixture was worked-up and finally distilled to obtain 15.2 g (yield: 71%) of 5-hexenyl chloride having a boiling point of 72° C./100 mmHg.

2) Synthesis of Diethyl 5-Hexenylmalonate

To 1000 ml of absolute ethanol was added 4 g (0.174 mole) of sodium, and 20 g (0.125 mole) of diethyl malonate was then added thereto. Further, 14 g (0.118 mole) of 5-hexenyl chloride as obtained in (1) above was slowly added thereto, followed by refluxing for 2 hours. The reaction mixture was freed of the solvent by distillation, and the residue was distilled to obtain 23.2 g (yield: 81%) of diethyl 5-hexenylmalonate having a boiling point of 115°–116° C./3 mmHg.

3) Hydrolysis and Decarboxylation

To 11 g (0.046 mole) of diethyl 5-hexenylmalonate as obtained in (2) above was added dropwise 35 ml of a 10% potassium hydroxide aqueous solution over a period of about 4 hours. After allowing the reaction mixture to stand overnight, 14 ml of diluted sulfuric acid (3%) was added thereto, and the mixture was refluxed for 5 hours. After cooling, the mixture was extracted with diethyl ether, and the solvent was removed by distillation. The residue was distilled to obtain 5.1 g (yield: 79%) of 7-octenoic acid as a colorless oil having a boiling point of 110°–112° C./5 mmHg.

4) Measurement of Physical Properties

Physical properties of the resulting 7-octenoic acid were measured with the same measuring instruments as used in Synthesis Example 1.

IR (KBr) cm$^{-1}$: 2900, 1705, 1640, 1410, 1280, 995, 910 $^1$H-NMR (CDCl$_3$) δ ppm: 1.1–1.8 (6H, m), 1.8–2.6 (4H, m), 4.8–5.2 (2H, m), 5.5–6.2 (1H, m), 11.23 (1H, brs)

MS (m/e): 142 (M+), 96, 74, 73, 69, 68, 60, 55, 43, 41

CNV TEST EXAMPLE

Influences of 3-methyl-2-hexenoic acid and 7-octenoic acid on CNV were examined in accordance with the above-described Fukuda's method.

i) Panel members 5 healthy adult males and 5 healthy adult females.

ii) Test Method

Smelling bottles containing filter paper to which a test compound was adhered or non-stimulating odorless filter (blank) were prepared. Electrodes for CNV recording were placed on predetermined sites of panel members. While recording electroencephalograms, vertical oculogyration, and respirations, panel members were made to sniff at the smelling bottle, and responses to a sound stimulus were recorded. A percentage of the sum of CNV of from 400 to 1000 msec from the sound stimulation when the test compound was given a sniff to that of the blank was obtained.

iii) Test Results

3-Methyl-2-hexenoic acid

Four out of the five males showed values higher than 100%, while four out of the five females showed values lower than 100%, indicating that 3-methyl-2-hexenoic acid gives an awakening effect to males and a sedative effect to females.

7-Octenoic acid

Four out of the five males showed values lower than 100%, while four out of the five females showed values higher than 100%, indicating that 7-octenoic acid gives a sedative effect to males and an awakening effect to females.

It was thus proved that 3-methyl-2-hexenoic acid and 7-octenoic acid give males and females a sedative effect and an awakening effect in an entirely opposite mode according to the sex.

CNV TEST REFERENCE EXAMPLE

Influences of androstenol and androsterone which are male hormones having a steroid skeleton and are also isolated from perspiration or urine on CNV were examined in the same manner as in CNV Test Example described above.

i) Panel members 5 healthy adult males and 5 healthy adult females.

ii) Test Results

Androstenol

All the five males showed values lower than 100%, while four out of the five females showed values higher than 100%, indicating that androstenol gives a sedative effect to males and an awakening effect to females.

Androsterone

Males showed no specific tendency, while all the five females showed 100% or lower values, indicating that androsterone gives a sedative effect to females.

It can be seen from these results that 3-methyl-2-hexenoic acid and 7-octenoic acid, though having no hormonal activity, give humans psychological effects similar to those produced on smelling male hormones, e.g., androstenol and androsterone. More specifically, 7-octenoic acid is expected to give males and females psychological effects similar to androstenol, while 3- methyl-2-hexenoic acid is expected to give females psychological effects similar to androsterone.

EXAMPLE 1

An animal base as a perfume composition having an animal tone was prepared according to the following formulation. The resulting perfume composition had an animal-like, and particularly civet- and musk-like keynote with a floral scent.

| Formulation: | |
| --- | --- |
| Benzyl phenylacetate | 75 parts |
| p-Cresyl phenylacetate | 25 parts |
| Phenylacetic acid | 1 part |
| 10-Undecenal | 3 parts |
| Indole | 5 parts |
| Linalool | 27 parts |
| α-Hexylcinnamic aldehyde | 25 parts |
| Cresyl acetate | 340 parts |
| p-Cresyl octanoate | 20 parts |
| Undecyl alcohol | 5 parts |
| Castreum absolute | 12 parts |
| Cistus labdanum | 3 parts |
| Sandalwood oil | 15 parts |
| Cardamom oil | 8 parts |
| Ethylene brassylate | 200 parts |
| Benzyl benzoate | 233 parts |
| 3-Methyl-2-hexenoic acid obtained in Synthesis Example 1 | 2 parts |
| 7-Octenoic acid obtained in Synthesis Example 2 | 1 part |
| | Total: 1000 parts |

The resulting animal base perfume composition was evaluated for its tastiness by organoleptic test by 30 specialized panel members in comparison with a perfume composition having the same formulation except for excluding 3-methyl-2-hexenoic acid and 7-octenoic acid. As a result, 22 out of 30 panel members answered that they preferred the perfume composition containing 3-methyl-2-hexenoic acid and 7-octenoic acid according to the present invention.

EXAMPLE 2

An animal base perfume composition was prepared in the same manner as in Example 1, except for replacing the 3-methyl-2-hexenoic acid and 7-octenoic acid with 3 parts of 3-methyl-2-hexenoic acid. The perfume composition had an animal keynote, particularly a civet- and musk-like keynote with a fatty and floral scent.

EXAMPLE 3

A perfume composition for fine fragrances was prepared according to the following formulation. This composition had a green floral keynote with a woody and musk-like scent.

| Formulation: | |
| --- | --- |
| Ethylene brassylate | 70 parts |
| Decyl aldehyde | 1 part |
| β-Damascon 10% triethyl citrate | 15 parts |
| Benzyl acetate | 40 parts |
| Benzyl salicylate | 125 parts |
| Cis-3-hexenyl salicylate | 30 parts |
| Eugenol | 40 parts |

| -continued | |
| --- | --- |
| Formulation: | |
| Piperonal | 45 parts |
| Indole | 2 parts |
| Ionone | 80 parts |
| Acetyl cedrene | 135 parts |
| Jasmine absolute | 5 parts |
| p-t-Butyl-α-methylhydrocinnamic aldehyde | 165 parts |
| Linalool | 85 parts |
| Orris concentrate 15% | 1 part |
| Rose oil | 20 parts |
| Terpineol | 50 parts |
| Vanillin | 2 parts |
| Citronellol | 88.7 parts |
| 3-Methyl-2-hexenoic acid obtained in Synthesis Example 1 | 0.2 part |
| 7-Octenoic acid obtained in Synthesis Example 2 | 0.1 part |
| | Total: 1000 parts |

The resulting animal base perfume composition was evaluated for its tastiness by organoleptic test by 30 specialized panel members in comparison with a perfume composition having the same formulation except for excluding 3-methyl-2-hexenoic acid and 7-octenoic acid. As a result, 21 out of 30 panel members answered that they preferred the perfume composition containing 3-methyl-2-hexenoic acid and 7-octenoic acid according to the present invention.

EXAMPLE 4

A perfume composition for fine fragrances was prepared in the same manner as in Example 3, except for replacing the 3-methyl-2-hexenoic acid and 7-octenoic acid with 0.3 part of 7-octenoic acid. The perfume composition had a floral keynote with a woody, fatty and muck-like scent.

As described above, the present invention provides a perfume composition containing 3-methyl-2-hexenoic acid and/or 7-octenoic acid which offers a fresh, natural, diffusible and highly tasty animal note without using animals. The perfume composition of the present invention has outstanding characteristics of giving humans an awakening effect and/or a sedative effect similar to some kinds of hormones. Hence, the perfume composition of the present invention is expected to find effective use in a broad range of applications, such as perfuming cosmetics, sanitary goods, and aromatherapy.

While the invention has been described in detail and with reference to specific examples thereof, it will be apparent to one skilled in the art that various changes and modifications can be made therein without departing from the spirit and scope thereof.

What is claimed is:
1. A perfume composition having an animal note, which comprises
   (a) a perfume material selected from the group consisting of synthetic perfumes, natural perfumes, synthetic essential oils and natural essential oils; and
   (b) from 0.001 to 2% by weight of 3-methyl-2-hexenoic acid and/or 7-octenoic acid, based on the whole perfume composition.
2. A perfume composition as in claim 1, wherein said synthetic perfumes, natural perfumes, synthetic essential oils, or natural essential oils have an animal, amber or balsam fragrance.

* * * * *